(12) United States Patent
Kim et al.

(10) Patent No.: US 11,752,060 B2
(45) Date of Patent: Sep. 12, 2023

(54) LINK ASSEMBLY AND MOTION ASSISTANCE APPARATUS INCLUDING THE SAME

(71) Applicant: Samsung Electronics Co., Ltd., Suwon-si (KR)

(72) Inventors: Jeonghun Kim, Suwon-si (KR); Minhyung Lee, Seoul (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 770 days.

(21) Appl. No.: 16/674,503

(22) Filed: Nov. 5, 2019

(65) Prior Publication Data

US 2020/0191208 A1 Jun. 18, 2020

(30) Foreign Application Priority Data

Dec. 12, 2018 (KR) .......................... 10-2018-0160124

(51) Int. Cl.
*A61H 3/00* (2006.01)
*A61F 2/66* (2006.01)

(52) U.S. Cl.
CPC ............. *A61H 3/00* (2013.01); *A61F 2/6607* (2013.01); *A61H 2003/007* (2013.01);
(Continued)

(58) Field of Classification Search
CPC ...... F16D 3/223; A61F 2/6607; A61F 5/0111; A61F 2005/0155; A61F 5/0127; A61F 2005/0165; A61F 2005/0146; A61F 5/0193; A61F 5/0102; A61F 2/60; A61F 2/66; A61H 3/00; A61H 2201/1481; A61H 2201/1642; A61H 2201/1673; A61H 2001/027; A61H 2201/0192; A61H 2201/0196; A61H 2201/1215; A61H 2201/1246; A61H 2201/149;
(Continued)

(56) References Cited

U.S. PATENT DOCUMENTS

| 4,112,709 A | 9/1978 | Krude |
| 6,497,548 B1 | 12/2002 | Roy et al. |

(Continued)

FOREIGN PATENT DOCUMENTS

| CN | 103006302 A | 4/2013 |
| CN | 107595546 A | 1/2018 |

(Continued)

OTHER PUBLICATIONS

Zong, Guanghua et al., "Classification and type synthesis of 1-DOF remote center of motion mechanisms," Mechanism and Machine Theory 43 (2008) 1585-1595, Elsevier Ltd., doi:10.1016/j.mechmachtheory.2007.12.008.

(Continued)

*Primary Examiner* — Justine R Yu
*Assistant Examiner* — Benjamin M. Kusiak
(74) *Attorney, Agent, or Firm* — HARNESS, DICKEY & PIERCE, P.L.C.

(57) ABSTRACT

A link assembly includes a main frame, a base link rotatably connected to the main frame, an input link rotatably connected to the main frame, and an output link at least 2-degree of freedom (DOF) rotatably connected to the main frame.

17 Claims, 13 Drawing Sheets

(52) U.S. Cl.
CPC ............... *A61H 2201/0157* (2013.01); *A61H 2201/1215* (2013.01); *A61H 2201/1436* (2013.01); *A61H 2201/1481* (2013.01); *A61H 2201/164* (2013.01); *A61H 2201/165* (2013.01); *A61H 2201/1642* (2013.01); *A61H 2201/1673* (2013.01); *A61H 2201/1676* (2013.01); *A61H 2201/5007* (2013.01); *A61H 2203/0406* (2013.01); *A61H 2205/106* (2013.01); *A61H 2205/12* (2013.01)

(58) Field of Classification Search
CPC ........ A61H 2201/164; A61H 2201/165; A61H 2201/1671; A61H 2201/5005; A61H 2201/5007; A61H 2201/5064; A61H 2201/5069; A61H 2203/0406; A61H 2205/10; A61H 1/0266; A61H 1/0262; A61H 2201/14; A61H 2201/1676; A61H 1/00; A61H 1/0237; A61H 3/008; A61H 2001/0207; A61H 2003/007; A61H 2201/12; A61H 2201/1207; A61H 2201/123; A61H 2201/5079; A61H 2201/0157; A61H 2201/0176; A61H 2201/1436; A61H 2201/1454; A61H 2205/106; A61H 2205/12; F16H 21/52; F16H 21/50; F16H 37/16; B25J 9/0006; A61B 17/64; Y10T 403/32606; Y10T 403/32631
USPC .......................................................... 601/27
See application file for complete search history.

(56) References Cited

U.S. PATENT DOCUMENTS

| 7,507,215 | B2* | 3/2009 | Ryan ..................... A61F 5/0123 602/26 |
| 7,632,188 | B2 | 12/2009 | Gleasman et al. |
| 10,441,439 | B2* | 10/2019 | Goldfarb ................... A61F 2/60 |
| 10,610,384 | B2* | 4/2020 | Byars ........................ A61F 2/66 |
| 2001/0002964 | A1* | 6/2001 | Song ....................... F16C 11/06 403/170 |
| 2005/0111907 | A1* | 5/2005 | Urbach ............... F16C 11/0604 403/122 |
| 2015/0321340 | A1* | 11/2015 | Smith ................... A61H 1/0244 74/490.01 |
| 2017/0181803 | A1* | 6/2017 | Mayer-Ullmann .... A61B 90/11 |
| 2017/0319205 | A1 | 11/2017 | Beardsley |
| 2018/0116826 | A1* | 5/2018 | Byars ..................... A61F 2/6607 |
| 2018/0177664 | A1 | 6/2018 | Choi et al. |
| 2018/0318122 | A1* | 11/2018 | LeCursi .................. A61F 5/0102 |
| 2018/0325766 | A1* | 11/2018 | Arzanpour ........... A61B 5/4528 |
| 2020/0016020 | A1* | 1/2020 | Mooney ............... A61B 5/6807 |
| 2020/0238542 | A1* | 7/2020 | Castro .................... B25J 9/0006 |
| 2021/0113415 | A1* | 4/2021 | Seifert ..................... A61H 3/00 |

FOREIGN PATENT DOCUMENTS

| JP | 2008539925 A | 11/2008 |
| KR | 2018-0023708 A | 3/2018 |
| WO | WO-2017/120680 A1 | 7/2017 |

OTHER PUBLICATIONS

Extended European Search Report dated May 4, 2020 for the corresponding European Application No. 19214211.5.

* cited by examiner

LINK ASSEMBLY AND MOTION ASSISTANCE APPARATUS INCLUDING THE SAME

CROSS-REFERENCE TO RELATED APPLICATION

This application claims priority under 35 U.S.C. § 119 to Korean Patent Application No. 10-2018-0160124, filed on Dec. 12, 2018, in the Korean Intellectual Property Office, the entire contents of which are incorporated herein by reference in their entirety.

BACKGROUND

1. Field

At least one example embodiment relates to a link assembly and/or a motion assistance apparatus including the same.

2. Description of the Related Art

A link assembly includes a plurality of links connected through a joint. The link assembly may be used to transmit a power. For example, a motion assistance apparatus enabling the elderly and/or patients having difficulties in walking may include the link assembly to transmit a power.

SUMMARY

Some example embodiments relate to a link assembly.

In some example embodiment, the link assembly may include a main frame; a base link rotatably connected to the main frame; an input link rotatably connected to the main frame; and an output link connected to the main frame such that the output link is configured to perform at least 2-degree of freedom (DOF) rotation with respect to the main frame.

In some example embodiments, a center of rotation of the output link is inside of the main frame.

In some example embodiments, the output link includes an output head connected to an interior of the main frame in a ball joint manner; and an output body extending from the output head.

In some example embodiments, an axis of rotation of the main frame with respect to the base link passes through a center of rotation of the output link, and an axis of rotation of the main frame with respect to the input link passes through the center of rotation of the output link.

In some example embodiments, the link assembly further includes a rotary frame rotatably connected to an interior of the main frame, the rotary frame configured to rotatably support the output link.

Some other example embodiments relate to a link assembly.

In some example embodiments, the link assembly includes a base link including a base head; an input link connected to the base head, the input link configured to perform at least 2-degree of freedom (DOF) rotational motion about the base head; and an output link connected to the base link or the input link, the output link configured to perform at least 2-DOF rotational motion about the base head.

In some example embodiments, the input link includes an input head connected to the base head in a ball joint manner; and an input body extending from the input head.

In some example embodiments, the link assembly further includes a rotary frame rotatably connected to an interior of the input head, the rotary frame configured to rotatably support the output link.

In some example embodiments, the output link includes an output head connected to the base head or the input head in a ball joint manner; and an output body extending from the output head.

In some example embodiments, an outermost head among the base head, the input head, and the output head has two opening halls, and a middle head among the base head, the input head, and the output head has a single opening hall.

Some example embodiments relate to a motion assistance apparatus.

In some example embodiments, the motion assistance apparatus includes a proximal support configured to support a proximal part of a user; a distal support configured to support a distal part of the user; a driver connected to the proximal support; and a link assembly configured to transmit a power from the driver to the distal support. In some example embodiments, the link assembly includes a main frame, a base link rotatably connected to the main frame, an input link rotatably connected to the main frame, and an output link connected to the main frame such that the output link is configured to perform at least 2-degree of freedom (DOF) rotation with respect to the main frame.

In some example embodiments, the base link incudes a first end rotatably connected to the proximal support and a second end rotatably connected to the main frame, the input link includes a first end configured to receive the power from the driver and a second end rotatably connected to the main frame, and the output link includes a first end rotatably connected to the main frame and a second end connected to the distal support.

In some example embodiments, wherein the link assembly further includes a fixed link fixed to the proximal support, the fixed link configured to rotatably support the base link; a connecting link between the fixed link and the main frame, the connecting link rotatably connected to the base link; and an auxiliary link rotatably connected to the fixed link and the connecting link.

In some example embodiments, the distal support is configured to rotate about a remote center of motion (RCM).

In some example embodiments, a center of rotation of the output link with respect to the main frame is inside of the main frame.

In some example embodiments, the output link includes an output head connected to the main frame in a ball joint manner; and an output body extending from the output head.

In some example embodiments, the link assembly further includes a rotary frame rotatably connected to an interior of the main frame, the rotary frame configured to rotatably support the output link.

Some other example embodiments also relate to a motion assistance apparatus.

In some example embodiments, the motion assistance apparatus includes a proximal support configured to support a proximal part of a user; a distal support configured to support a distal part of the user; a driver connected to the proximal support; and a link assembly configured to transmit a power from the driver to the distal support, the link assembly including, a base link including a base head, an input link connected to the base head, the input link configured to perform an at least 2-degree of freedom (DOF) rotational motion about the base head, and an output link connected to the base link or the input link, the output link configured to perform an at least 2-DOF rotational motion about the base head.

In some example embodiments, the base link includes a first end rotatably connected to the proximal support, the input link includes a first end configured to receive the power received from the driver and a second end configured to perform the at least 2-degree of freedom (DOF) rotational motion about the base head, and the output link includes a first end connected to the base link or the input link and a second end connected to the distal support.

In some example embodiments, the input link includes an input head connected to the base head in a ball joint manner; and an input body extending from the input head.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
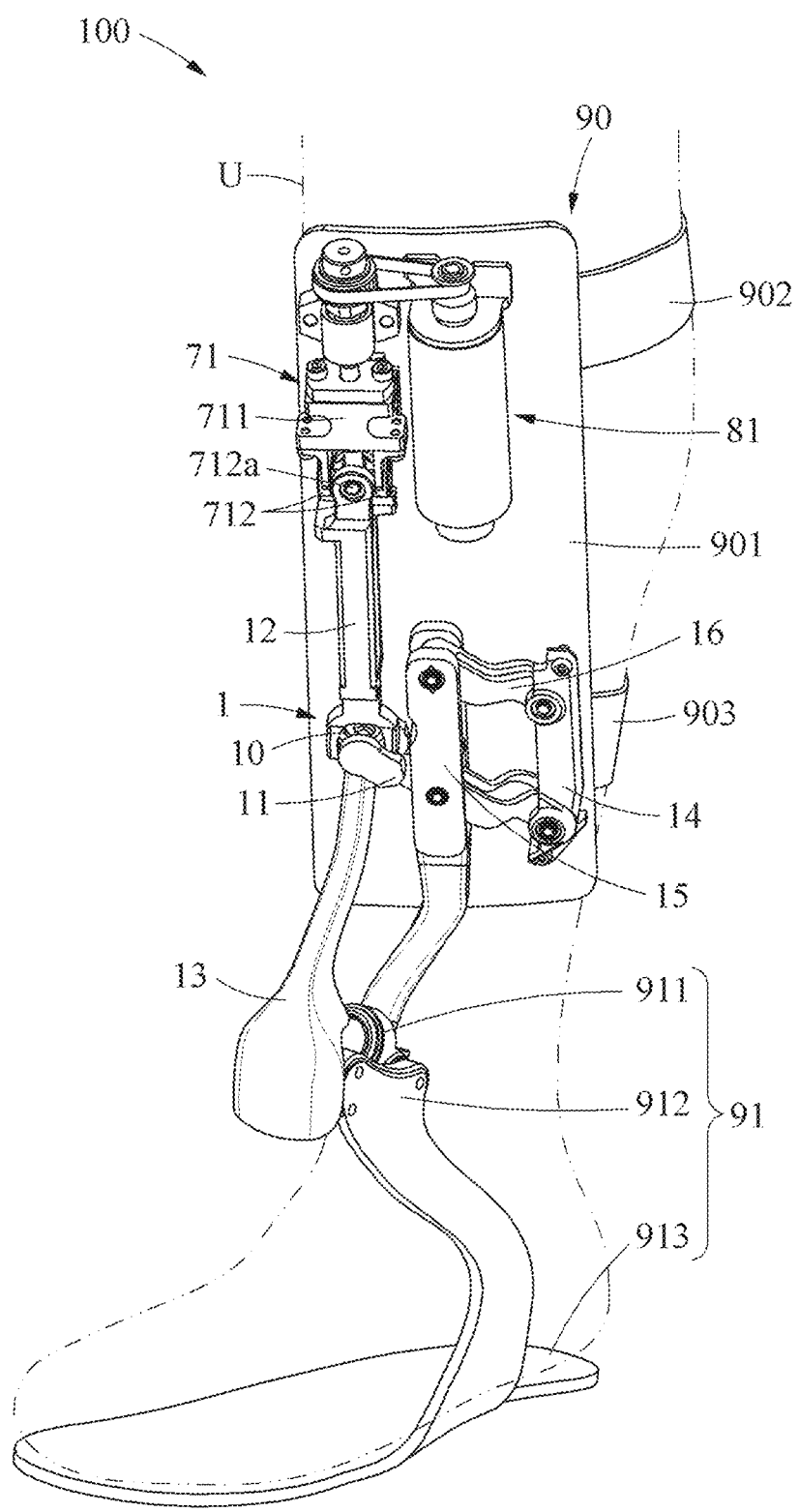
FIG. 1 is a perspective view illustrating a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 2:
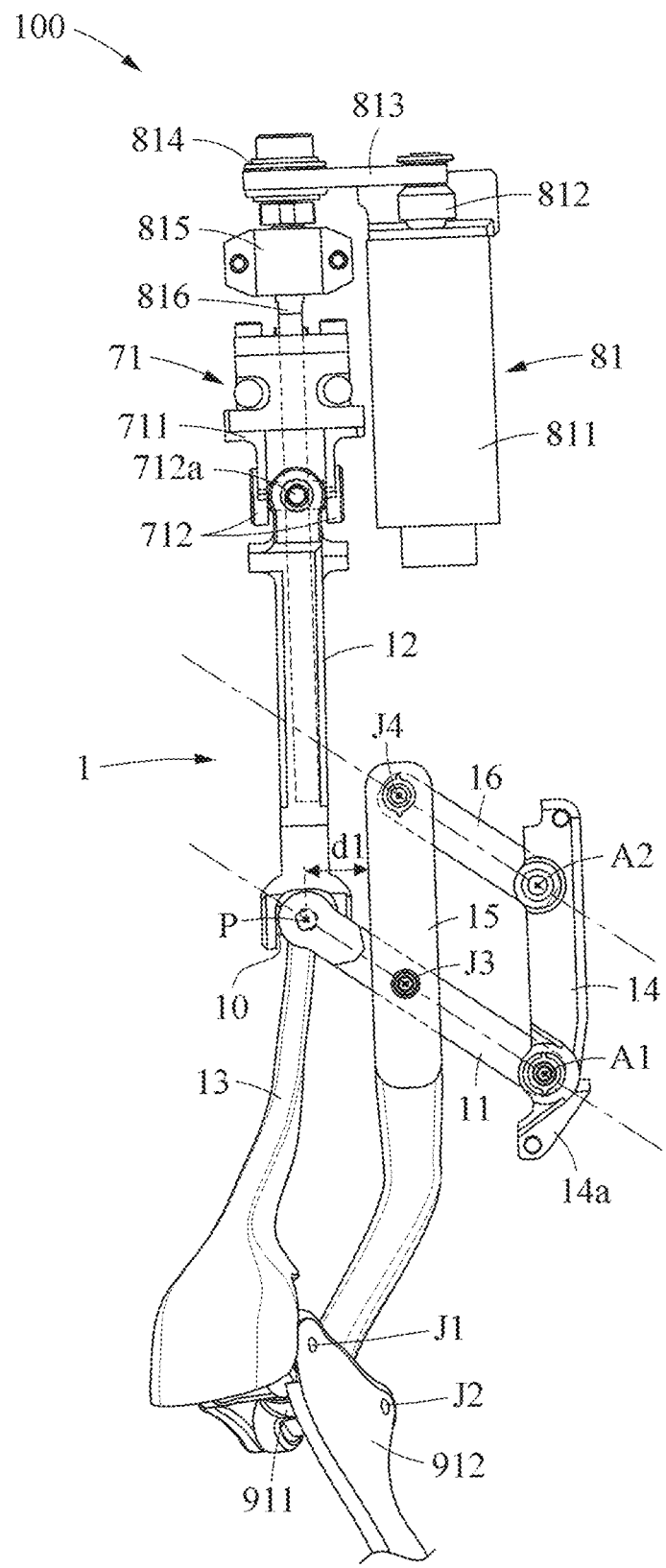
FIGS. 2 through 4 are top views illustrating a motion assistance apparatus according to at least one example embodiment.
Figure 3:
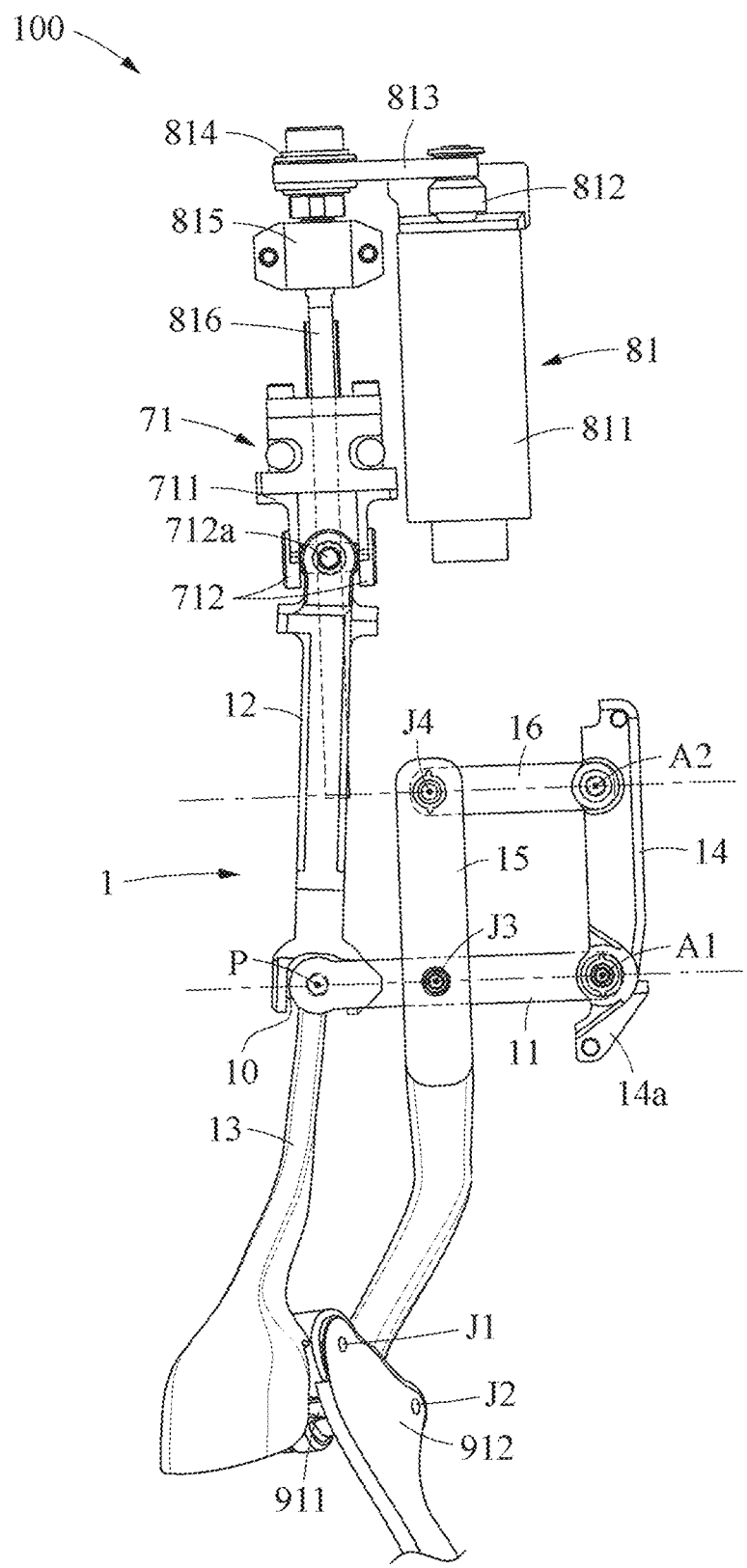
Figure 4:
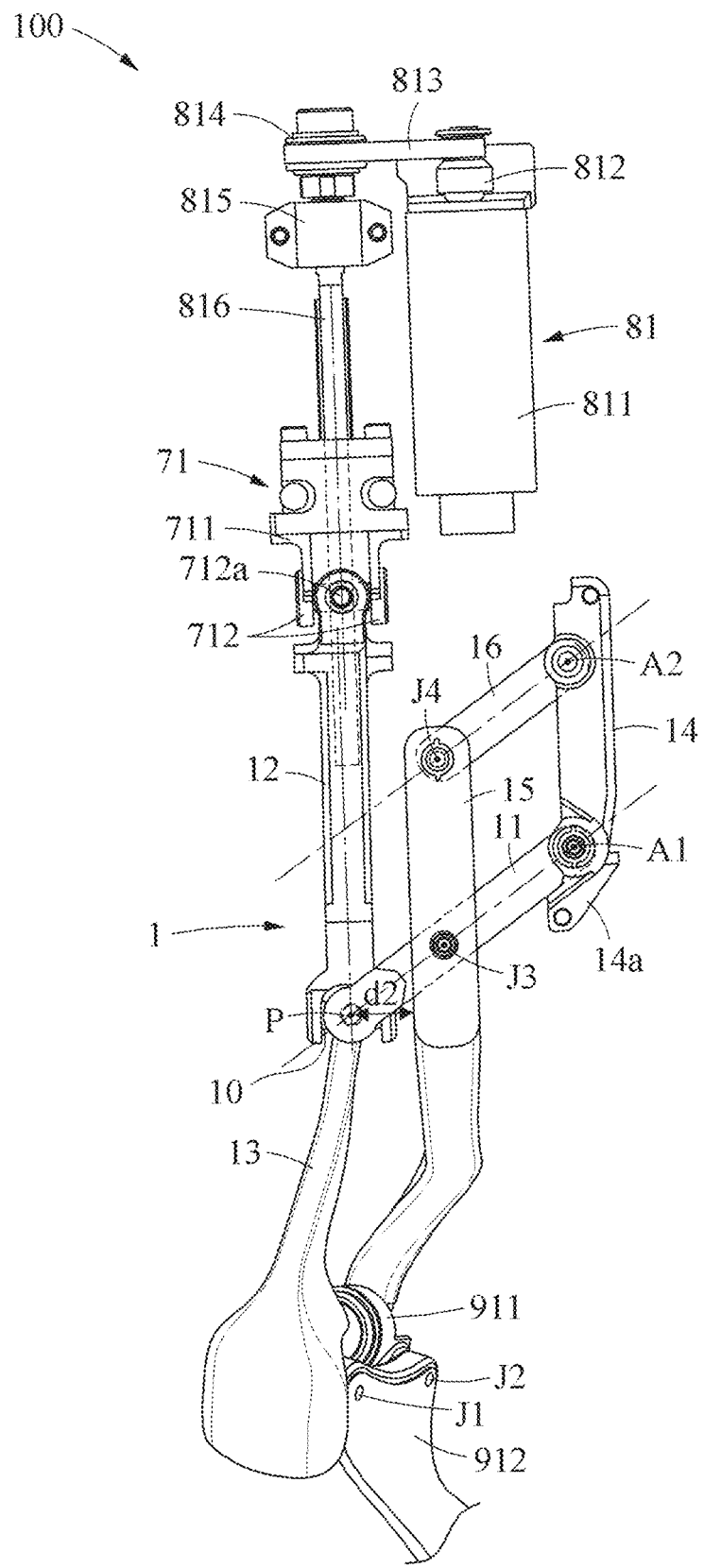
Figure 5:
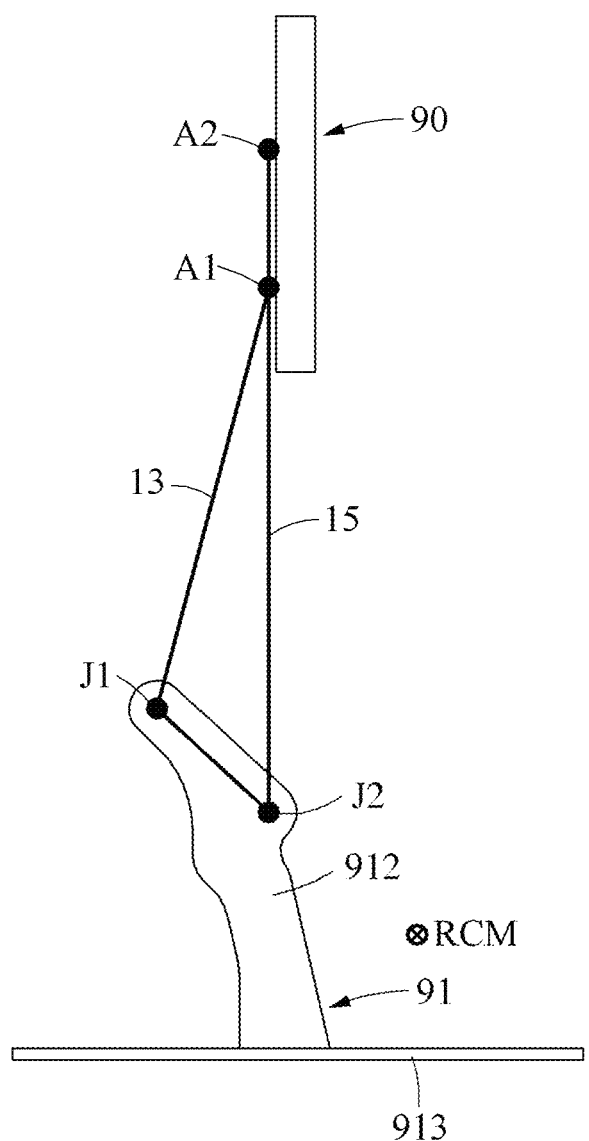
FIGS. 5 and 6 are side views illustrating a motion assistance apparatus according to at least one example embodiment.
Figure 6:
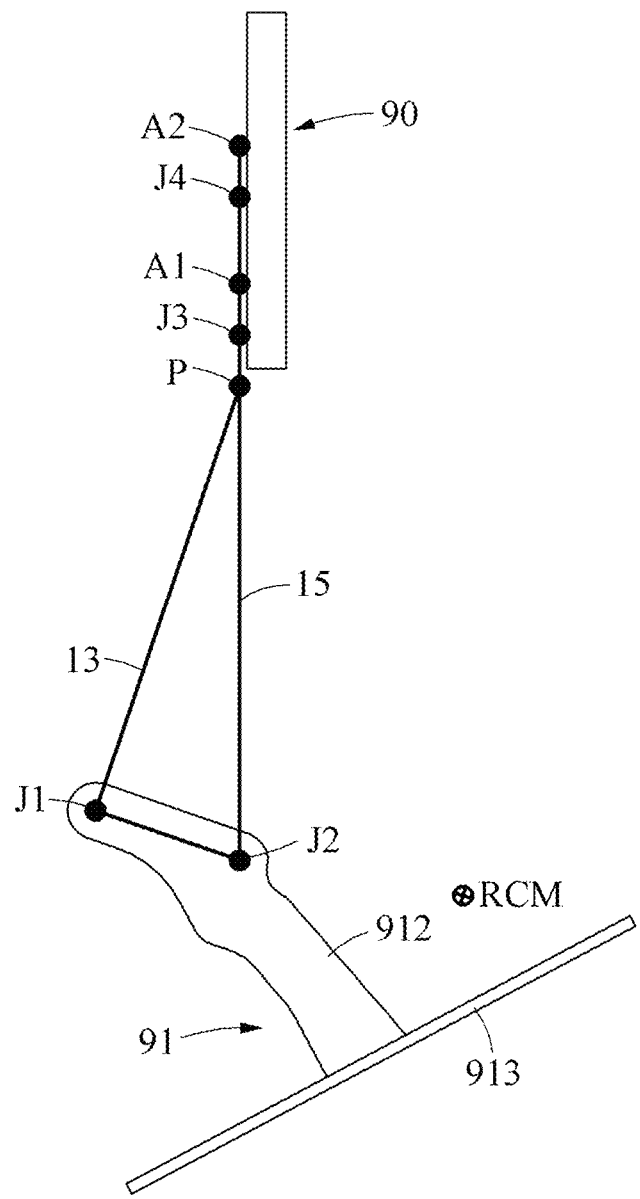

FIG. 1 is a perspective view illustrating a motion assistance apparatus according to at least one example embodiment, FIGS. 2 through 4 are top views illustrating the motion assistance apparatus according to at least one example embodiment, and FIGS. 5 and 6 are side views illustrating the motion assistance apparatus according to at least one example embodiment.

Referring to FIGS. 1 through 6, a motion assistance apparatus 100 may be worn by a user U and assist a joint of the user, for example, a talocrural joint, a knee joint, a hip joint, a wrist joint, or an elbow joint. The user may correspond to a human, an animal, or a robot. The motion assistance apparatus 100 may include a link assembly 1, a slider 71, a driver 81, a proximal support 90, and a distal support 91.

The proximal support 90 may support a proximal part of the user, and the distal support 91 may support a distal part of the user. The motion assistance apparatus 100 may assist a motion of the joint of the user by adjusting an angle between the proximal support 90 and the distal support 91. For example, the proximal support 90 may support a shank of the user, and the distal support 91 may support a foot of the user, whereby the motion assistance apparatus 100 may assist a plantar flexion and/or a dorsi flexion of the talocrural joint of the user. Hereinafter, the motion assistance apparatus 100 assisting the talocrural joint of the user will be principally described. However, example embodiments are not limited thereto. For example, the proximal support 90 may support a forearm of the user, and the distal support 91 may support a palm of the user, whereby the motion assistance apparatus 100 may assist the wrist joint of the user.

The proximal support 90 may support the shank of the user. The proximal support 90 may include a proximal supporting plate 901 attached to the shank of the user, and proximal supporting bands 902 and 903 connected to the proximal supporting plate 901, the proximal supporting bands 902 and 903 enclosing a calf of the user. At least two proximal supporting bands 902 and 903 may be provided to be spaced apart from each other in a longitudinal direction of the calf of the user. The first proximal supporting band 902 may prevent a downward separation of the motion assistance apparatus 100, and the second proximal supporting band 903 may prevent an upward separation of the motion assistance apparatus 100. Lengths of the proximal supporting bands 902 and 903 may be adjustable.

The distal support 91 may support the foot of the user. The distal support 91 may include a distal supporting joint 911 rotatably connected to a connecting link 15, a distal connecting frame 912 connecting the distal supporting joint 911 and an output link 13 and enclosing at least a portion of an upper portion and a side portion of the foot of the user, and a distal supporting plate 913 supporting a sole of the foot of the user. The distal supporting joint 911 may assist an ankle of the user to freely perform an eversion and/or an inversion about a subtalar joint of the user. The distal connecting frame 912 may be rotatably connected to the output link 13 about a first joint J1, and rotatably connected to the distal supporting joint 911 about a second joint J2. The first joint J1 and the second joint J2 may be joints implementing a 1-degree of freedom (DOF) rotational motion, for example, hinges.

The user may wear a shoe (not shown) over the motion assistance apparatus 100. At least a portion of the distal connecting frame 912 and the distal supporting plate 913 may be positioned in the shoe. In particular, the distal supporting plate 913 may be positioned between an insole of the shoe and the sole of the foot of the user. The distal supporting plate 913 may assist the plantar flexion by pushing the insole of the shoe, and assist the dorsi flexion by pushing the sole of the foot of the user.

The driver 81 may implement a relative motion of the distal support 91 with respect to the proximal support 90. The driver 81 may transmit a power to one link of the link assembly 1, for example, an input link 12. The driver 81 may include a driving motor 811 to generate the power, an output shaft 812 provided at one end of the driving motor 811 and configured to rotate using the power generated by the driving motor 811, a power transmitting belt 813 configured to transmit the power between the output shaft 812 and a rotor 814, the rotor 814 configured to be rotated by the power transmitting belt 813, a driving shaft 816 connected to a center of rotation of the rotor 814, and a shaft support 815 configured to support the driving shaft 816.

In some example embodiments, the motion assistance apparatus 1 may further include a controller (not shown) connected to the driver 81.

The controller may include a processor and a memory. The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The processor may processor may be an arithmetic logic unit, a digital signal processor, a microcomputer, a field programmable array, a programmable logic unit, a microprocessor or any other device capable of responding to and executing instructions in a defined manner. The memory may contain computer readable code that, when executed by the processor, configures the processor as a special purpose computer.

For example, the memory may contain computer readable code that, when executed by the processor, configures the processor as a special purpose computer to control the driver 81 to generate the power and transmit the same to the distal support 91 via the link assembly 1.

The slider 71 may be connected to the driving shaft 816 in a ball screw manner. The slider 71 may slide along the driving shaft 816. The slider 71 may slide in a direction toward the distal support 91 or in a direction away from the distal support 91. The slider 71 may include a slider body 711 connected to the driving shaft 816, and a slider head 712 rotatably connected to the slider body 711. The slider head 712 may rotate about, for example, an axis of rotation approximately parallel to the proximal supporting plate 901. The slider head 712 may include a supporting protrusion 712a configured to rotatably support the input link 12. The input link 12 may rotate about an axis of rotation approximately perpendicular to the axis of rotation of the slider head 712. The input link 12 may perform a 2-DOF rotational motion with respect to the slider body 711.

The link assembly 1 may transmit the power from the driver 81 to the distal support 91. The link assembly 1 may assist the distal support 91 to rotate about a remote center of motion (RCM). The distal support 91 may simultaneously perform a translational motion and a rotational motion with respect to the proximal support 90 by means of the link assembly 1. The link assembly 1 may include a main frame 10, a base link 11, the input link 12, the output link 13, a fixed link 14, the connecting link 15, and an auxiliary link 16.

The link assembly 1 may be applied to other apparatuses having a structure in which three links may rotate relatively, in addition to the motion assistance apparatus 100.

The main frame 10 may rotatably support the base link 11, the input link 12, and the output link 13. Axes of rotation of the base link 11 and the input link 12 may pass through the main frame 10. A center of rotation of the output link 13 may be formed at a point P inside of the main frame 10. The axes of rotation of the base link 11 and the input link 12 may pass through a vicinity of the point P. The axes of rotation of the base link 11 and the input link 12 may intersect at the point P.

When the intersection point of the axes of rotation of the base link 11 and the input link 12 is formed close to the center of rotation of the output link 13, the link assembly 1 may have a relatively great range of motion. The intersection point of the axes of rotation of the base link 11 and the input link 12 may match the center of rotation of the output link 13.

The base link 11 may be rotatably connected to the main frame 10 and the fixed link 14. The fixed link 14 may be fixed to the proximal supporting plate 901, which will be described later. For example, the fixed link 14 and the proximal supporting plate 901 may be formed as an integral body. The base link 11 may rotate about a first axis of rotation A1 on the fixed link 14. The main frame 10 may revolve about the first axis of rotation A1, and rotate about the base link 11.

One end of the input link 12 may move using the power received from the driver 81, and the other end of the input link 12 may be rotatably connected to the main frame 10. The input link 12 may be rotatably connected to the main frame 10 and the slider 71. The main frame 10 may revolve about the supporting protrusion 712a, and rotate about the input link 12. The input link 12 may be connected to the base link 11 through the main frame 10 in a universal joint manner. The input link 12 may perform a 2-DOF rotational motion with respect to the base link 11.

The output link 13 may be 2-DOF rotatably connected to the main frame 10. For example, the output link 13 may be connected to the main frame 10 in a ball joint manner. The center of rotation of the output link 13 may be formed inside of the main frame 10. The output link 13 may perform a 2-DOF rotational motion with respect to the base link 11 or the input link 12.

The base link 11 may perform an upward rotational motion until the base link 11 or the input link 12 is restricted by the connecting link 15, and perform a downward rotational motion until the base link 11 or the output link 13 is restricted by the connecting link 15. Since the center of rotation of the output link 13 is provided inside of the main frame 10 connecting the base link 11 and the input link 12, the base link 11, the input link 12, and the output link 13 may be connected in a compact structure, and thus a range of motion of the base link 11 may be extended. For example, a distance d1 of FIG. 2 between the point P and the connecting link 15 when the base link 11 rotates upward and a distance d2 of FIG. 4 between the point P and the connecting link 15 when the base link 11 rotates downward may be formed as close as possible.

The fixed link 14 may rotatably support the base link 11. The fixed link 14 may be fixed to the proximal supporting plate 901. The fixed link 14 may rotatably support the base link 11 and the auxiliary link 16. The base link 11 may rotate about the first axis of rotation A1 on the fixed link 14, and the auxiliary link 16 may rotate about a second axis of rotation A2 on the fixed link 14. The fixed link 14 may include a stopper 14a configured to prevent an excessive downward rotation of the base link 11. For example, the stopper 14a may prevent a collision between the input link 12 and the connecting link 15. The stopper 14a may include an elastic body (not shown) provided on a surface thereof facing the base link 11 to absorb an impact.

The connecting link 15 may be disposed between the fixed link 14 and the main frame 10, and rotatably connected to the base link 11 about a third joint J3. The connecting link 15 may be rotatably connected to the auxiliary link 16 about a fourth joint J4.

The auxiliary link 16 may be rotatably connected to the fixed link 14 and the connecting link 15. The base link 11, the fixed link 14, the connecting link 15, and the auxiliary link 16 may perform a 4-bar linkage motion. For example, the base link 11 may be parallel to the auxiliary link 16, and the fixed link 14 may be parallel to the connecting link 15.

The second joint J2 between the connecting link 15 and the distal support 91, the first axis of rotation A1 and the second axis of rotation A2 respectively corresponding to the axes of rotation of the base link 11 and the auxiliary link 16, the third joint J3 between the base link 11 and the connecting link 15, the fourth joint J4 between the auxiliary link 16 and the connecting link 15, and the point P corresponding to the center of rotation of the output link 13 may all be positioned on the same plane. Meanwhile, the first joint J1 between the output link 13 and the distal support 91 may be positioned in front of the plane.

A translational motion speed of the output link 13 may be determined based on a distance from the first axis of rotation A1 to the point P, and a translational motion speed of the connecting link 15 may be determined based on a distance from the second axis of rotation A2 to the fourth joint J4. Thus, the output link 13 may perform a translational motion faster than the connecting link 15. Since the first joint J1 performs a translational motion faster than the second joint J2, the distal support 91 may perform a rotational motion about the RCM.

Figure 7:
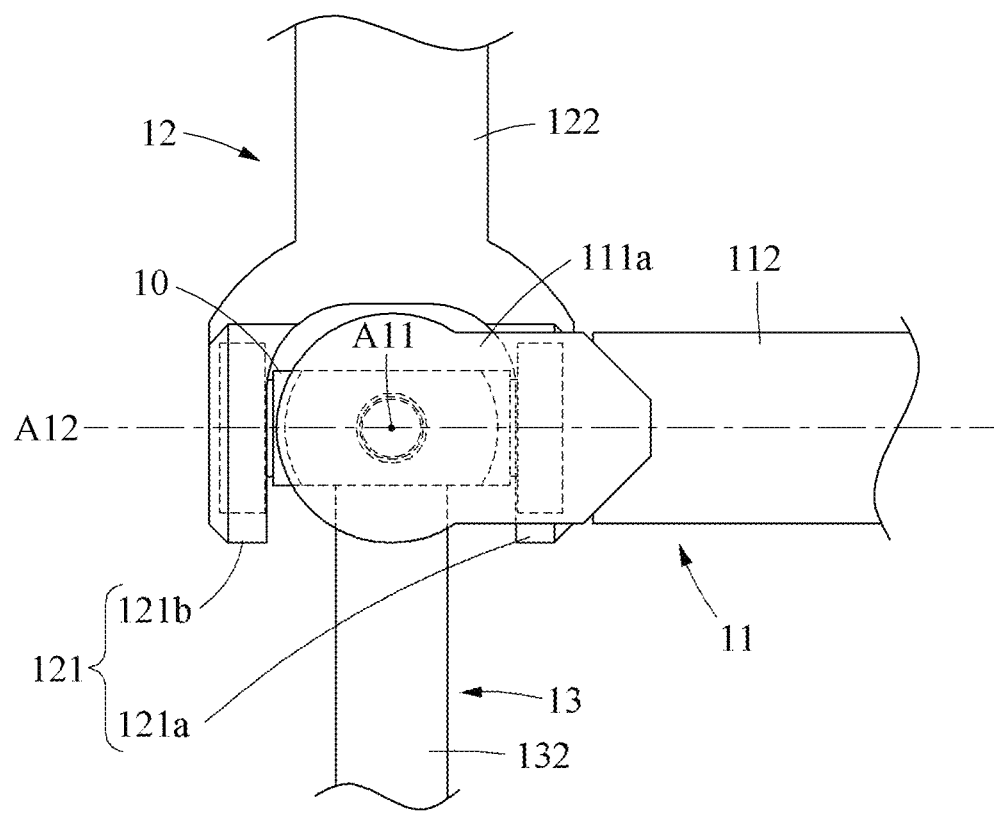
FIG. 7 is a top view illustrating a link assembly according to at least one example embodiment.
Figure 8:
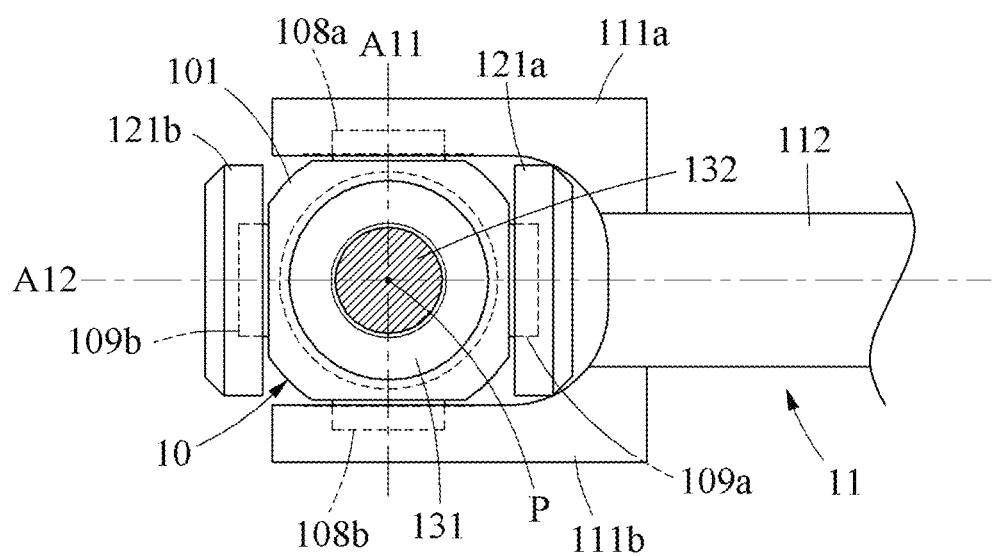
FIG. 8 is a front view illustrating the link assembly of FIG. 7.
Figure 9:
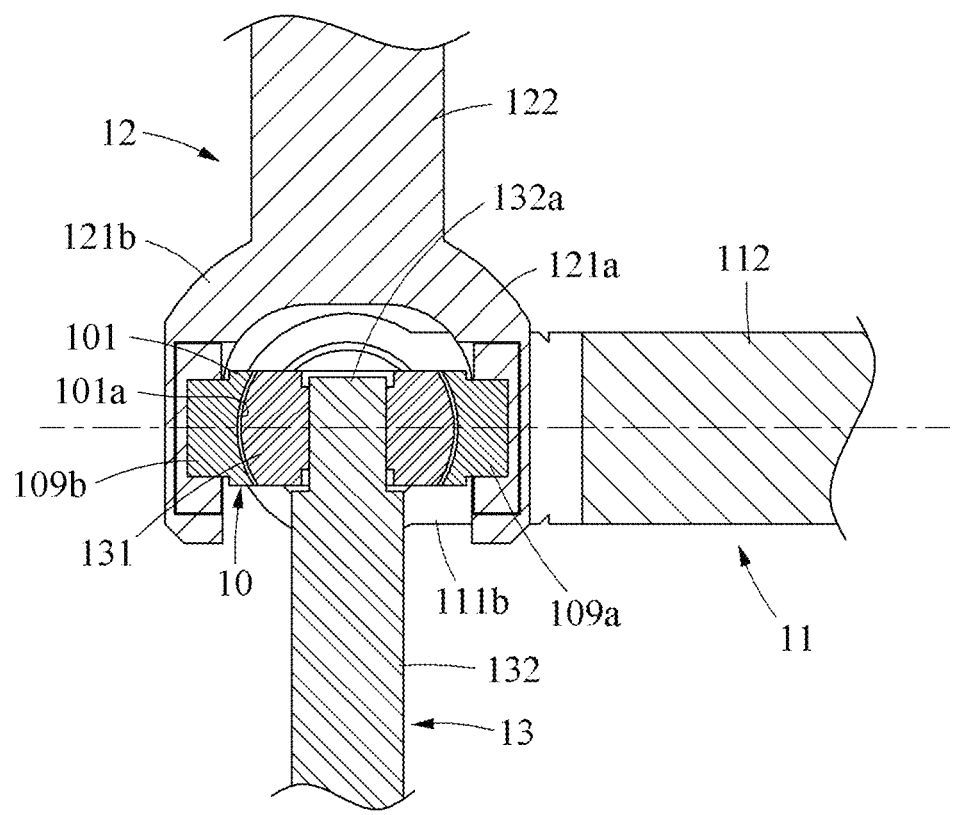
FIG. 9 is a cross-sectional view illustrating the link assembly of FIG. 7.

FIG. 7 is a top view illustrating a link assembly according to at least one example embodiment, FIG. 8 is a front view illustrating the link assembly of FIG. 7, and FIG. 9 is a cross-sectional view illustrating the link assembly of FIG. 7.

Referring to FIGS. 7 through 9, a universal joint may be formed outside of the link assembly 1, and a ball joint may be formed inside of the link assembly 1. The base link 11 and the input link 12 may be connected in a universal joint manner about the main frame 10. The output link 13 may be connected inside of the main frame 10 in a ball joint manner.

The main frame 10 may include a main frame body 101, and a plurality of main projections 108a, 108b, 109a, and 109b formed to protrude from the main frame body 101 in many directions.

A receiving space may be provided inside of the main frame body 101 to receive at least a portion of the output link 13. A gasket (not shown) to reduce a friction with the output link 13 may be provided on an inner wall of the main frame body 101. The main frame body 101 may include an opening hall enclosing the output link 13. For example, the point P corresponding to the center of rotation of the output link 13 may be positioned at a central portion of the main frame body 101.

The plurality of main projections 108a, 108b, 109a, and 109b may protrude from the main frame body 101. The plurality of main projections 108a, 108b, 109a, and 109b may include the first main projection 108a and the second main projection 108b to be inserted into the base link 11 to assist the main frame body 101 to rotate about a first axis A11 with respect to the base link 11. The plurality of main projections 108a, 108b, 109a, and 109b may further include the third main projection 109a and the fourth main projection 109b to be inserted into the input link 12 to assist the main frame body 101 to rotate about a second axis A12 with respect to the input link 12.

Although it has been described above that the plurality of main projections 108a, 108b, 109a, and 109b protrudes from the main frame body 101, example embodiments are not limited thereto. For example, the plurality of main projections 108a, 108b, 109a, and 109b may protrude from the base link 11 or the input link 12, and the main frame body 101 may include a receiving groove configured to receive the plurality of main projections 108a, 108b, 109a, and 109b.

The first axis A11 and the second axis A12 may intersect with each other inside of the main frame body 101. For example, the first axis A11 and the second axis A12 may intersect with each other at the point P corresponding to the center of rotation of the output link 13.

The base link 11 may include base heads 111a and 111b, and a base body 112 extending from the base heads 111a and 111b.

The base heads 111a and 111b may include the first base head 111a and the second base head 111b provided on opposite side from the main frame 10. The first base head 111a may rotatably support the first main projection 108a, and the second base head 111b may rotatably support the second main projection 108b.

The input link 12 may include an input head 121, and an input body 122 extending from the input head 121.

The input head 121 may include a first input head 121a and a second input head 121b provided on opposite sides from the main frame 10. The first input head 121a may rotatably support the third main projection 109a, and the second input head 121b may rotatably support the fourth main projection 109b.

The input body 122 and the base body 112 may extend in different directions. The input body 122 may perform a 2-DOF rotational motion about the base body 112.

The output link 13 may perform an at least 2-DOF rotational motion about the main frame 10. The center of rotation of the output link 13 may be formed at the point P inside of the main frame 10. The first axis A11 corresponding to the axis of rotation of the main frame 10 with respect to the base link 11 may pass through the point P corresponding to the center of rotation of the output link 13. Further, the second axis A12 corresponding to the axis of rotation of the main frame 10 with respect to the input link 12 may pass through the point P corresponding to the center of rotation of the output link 13. The output link 13 may include an output head 131 rollably disposed inside of the main frame 10, and an output body 132 extending from the output head 131.

The output head 131 may be connected inside of the main frame 10 in a ball joint manner. The output head 131 may be disposed in the receiving space of the main frame body 101. The output head 131 may approximately have a spherical shape. The output head 131 may support the output body 132. For example, the output head 131 may include a hall at a central portion thereof to support the output body 132. The output body 132 may be inserted into the hall of the output head 131.

The output body 132 may perform an at least 2-DOF rotational motion in the opening hall of the main frame body 101. For example, the output body 132 may rotate about the first axis A11, rotate about the second axis A12, or rotate about an axis perpendicular to the first axis A11 and the second axis A12. The output body 132 may include a body tip 132a to be inserted into the output head 131.

Figure 10:
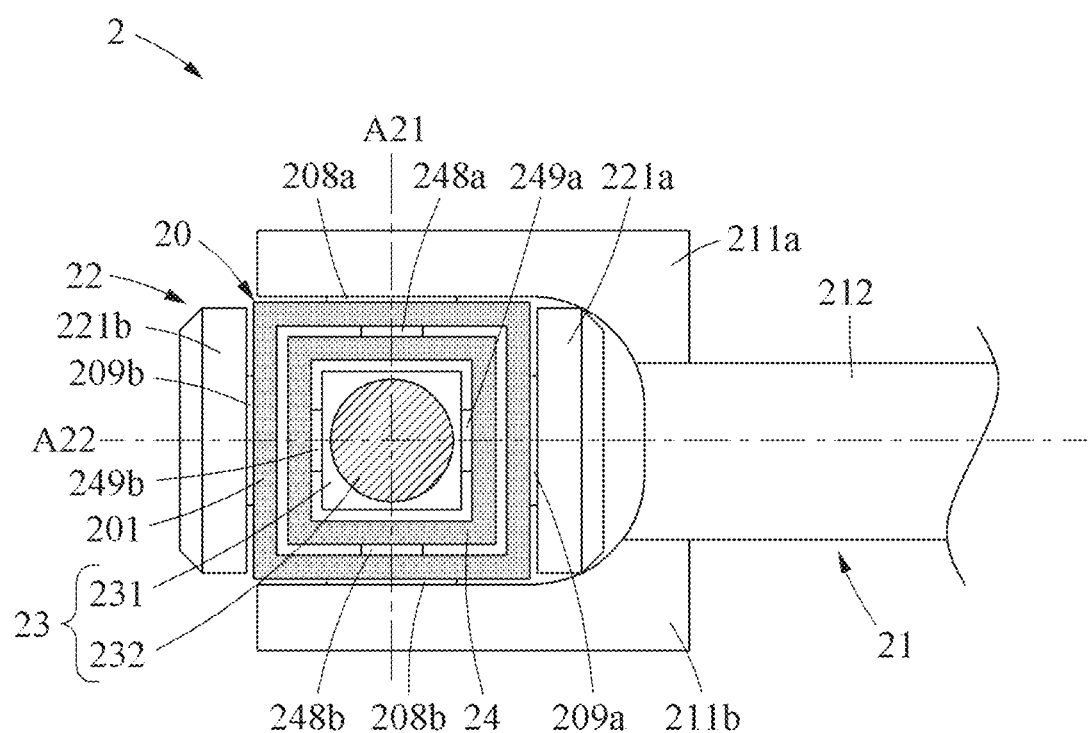
FIG. 10 is a front view illustrating a link assembly according to at least one example embodiment.

FIG. 10 is a front view illustrating a link assembly according to at least one example embodiment.

Referring to FIG. 10, a link assembly 2 may include a main frame 20, a base link 21, an input link 22, an output link 23, and a rotary frame 24.

The main frame 20 may include a main frame body 201, and a plurality of main projections 208a, 208b, 209a, and 209b formed to protrude from the main frame body 201 in many directions. The main frame body 201 may rotate about a first axis A21 and/or a second axis A22.

The base link 21 may include base heads 211a and 211b configured to rotatably support the main frame 20, and a base body 212 extending from the base heads 211a and 211b. The base heads 211a and 211b may include the first base head 211a and the second base head 211b provided on opposite sides from the main frame 20.

The input link 22 may be connected to the base link 21 through the main frame 20 in a universal joint manner. The input link 22 may include input heads 221a and 221b configured to rotatably support the main frame body 201, and an input body (not shown) extending from the input heads 221a and 221b. The input heads 221a and 221b may include the first input head 221a and the second input head 221b provided on opposite sides from the main frame 20.

The output link 23 may perform a 2-DOF rotational motion about the main frame 20. The output link 23 may be connected to the main frame 20 through the rotary frame 24 in a universal joint manner, which will be described below. The output link 23 may include an output head 231 rotatably connected to the rotary frame 24, and an output body 232 extending from the output head 231.

The rotary frame 24 may be provided inside of the main frame 20, and rotatably connected to the main frame 20. The rotary frame 24 may rotatably support the output link 23. For example, the rotary frame 24 may include a rotary frame body provided inside of the main frame 20, and a plurality of rotary projections 248a, 248b, 249a, and 249b formed to protrude from the rotary frame body.

The plurality of rotary projections 248a, 248b, 249a, and 249b may include the first rotary projection 248a and the second rotary projection 248b formed to protrude outward from the rotary frame body and rotatably inserted respectively into the first base head 211a and the second base head 211b. The plurality of rotary projections 248a, 248b, 249a, and 249b may further include the third rotary projection 249a and the fourth rotary projection 249b formed to protrude inward from the rotary frame body and configured to rotatably support the output head 231.

An axis of rotation of the rotary frame 24 being parallel to the first axis A21 is illustrated. However, example embodiments are not limited thereto. The axis of rotation of the rotary frame 24 may be inclined with respect to the first axis A21. Further, an axis of rotation of the output link 23 being parallel to the second axis A22 is illustrated. However, example embodiments are not limited thereto.

Figure 11:
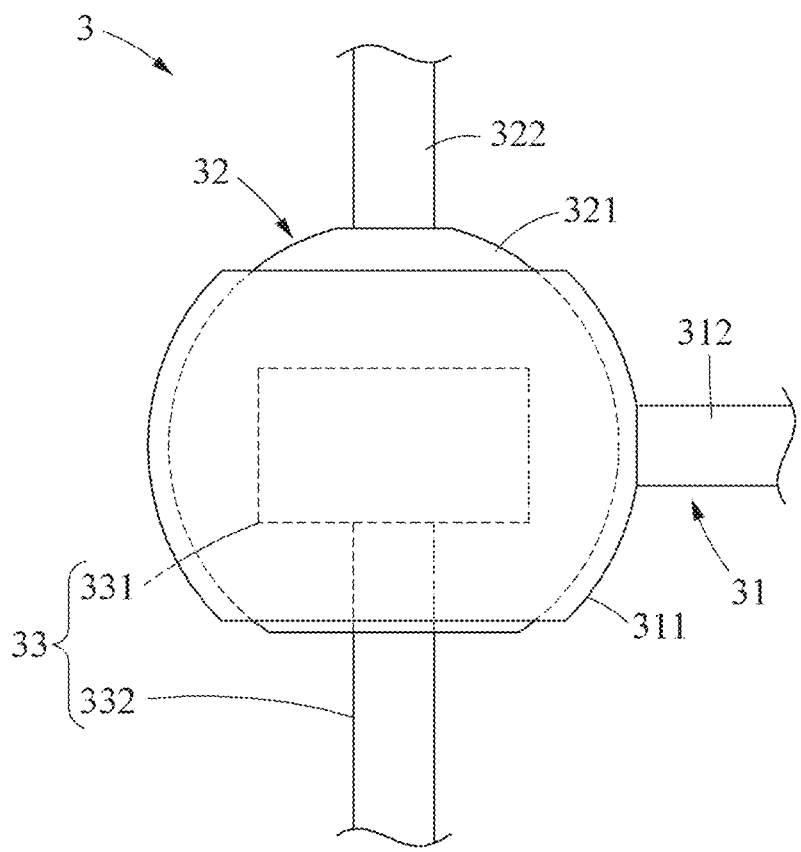
FIG. 11 is a top view illustrating a link assembly according to at least one example embodiment.
Figure 12:
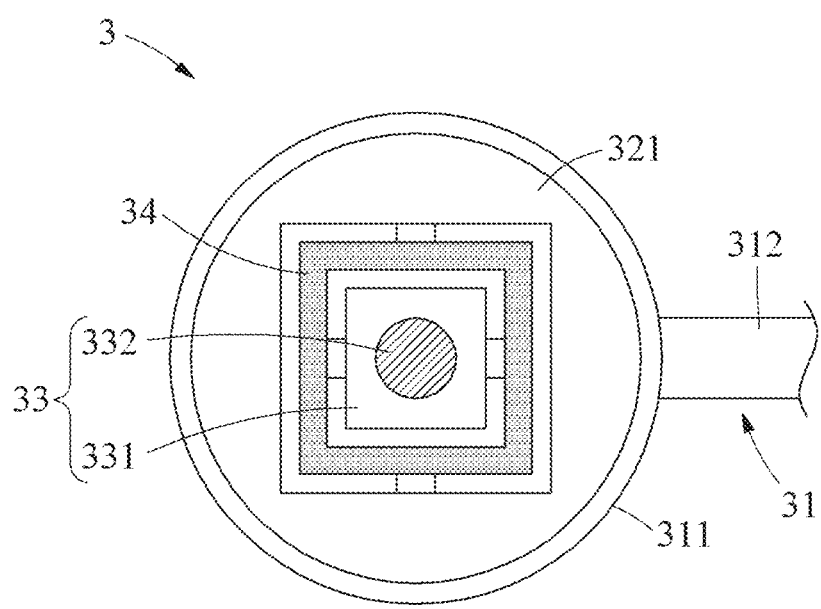
FIG. 12 is a front view illustrating the link assembly of FIG. 11.

FIG. 11 is a top view illustrating a link assembly according to at least one example embodiment, and FIG. 12 is a front view illustrating the link assembly of FIG. 11.

Referring to FIGS. 11 and 12, a link assembly 3 may include a base link 31, an input link 32, an output link 33, and a rotary frame 34. The base link 31 and the input link 32 may be connected in a ball joint manner, and the input link 32 and the output link 33 may be connected in a universal joint manner.

The base link 31 may include a base head 311 and a base body 312. The base head 311 may include a space to receive at least a portion of the input link 32. A gasket (not shown) to reduce a friction with the input link 32 may be provided on an inner wall of the base head 311.

The input link 32 may perform an at least 2-DOF rotational motion with respect to the base link 31. A center of rotation of the input link 32 may be positioned inside of the base head 311. The input link 32 may include an input head 321 connected to the base head 311 in a ball joint manner, and an input body 322 extending from the input head 321. The input head 321 may roll inside of the base head 311. The input head 321 may have an approximately spherical shape. The input head 321 may include a space to receive at least a portion of the output link 33.

The output link 33 may perform an at least 2-DOF rotational motion with respect to the input link 32. The output link 33 may include an output head 331 provided inside of the input head 321, and an output body 332 extending from the output head 331. The output link 33 may be connected to the input link 32 through the rotary frame 34 in a universal joint manner.

The rotary frame 34 may be provided inside of the input head 321, and rotatably connected to the input head 321. The rotary frame 34 may rotatably support the output link 33. The output link 33 may perform a 1-DOF rotational motion with respect to the rotary frame 34, and the rotary frame 34 may perform a 1-DOF rotational motion with respect to the input link 32, whereby the output link 33 may perform a 2-DOF rotational motion with respect to the input link 32.

Figure 13:
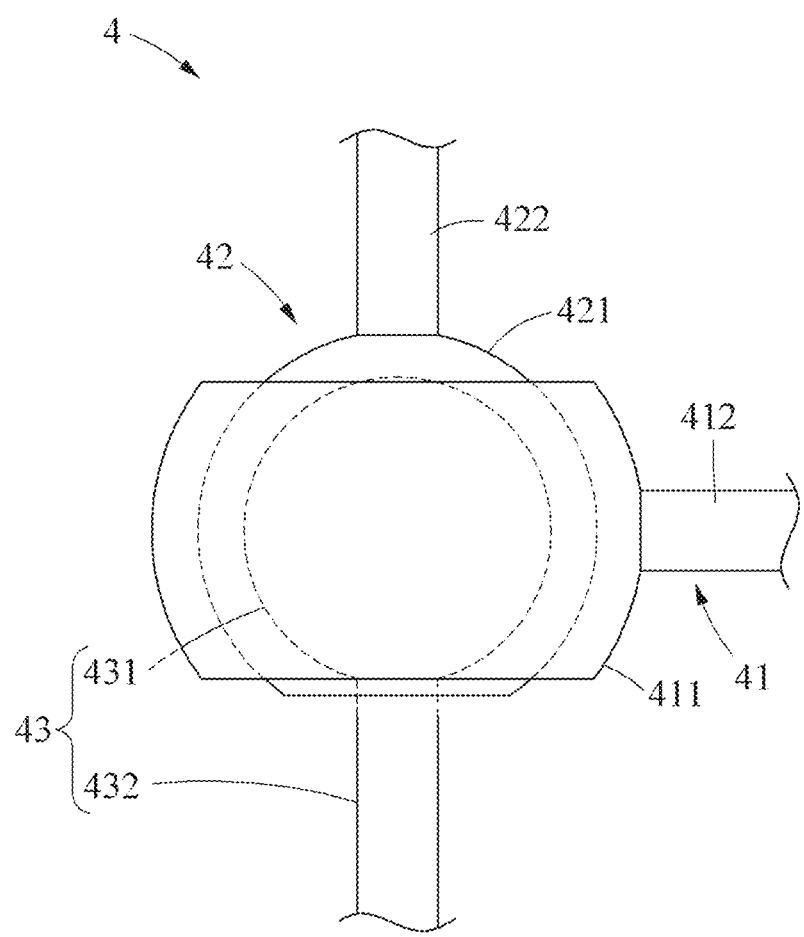
FIG. 13 is a top view illustrating a link assembly according to at least one example embodiment.
Figure 14:
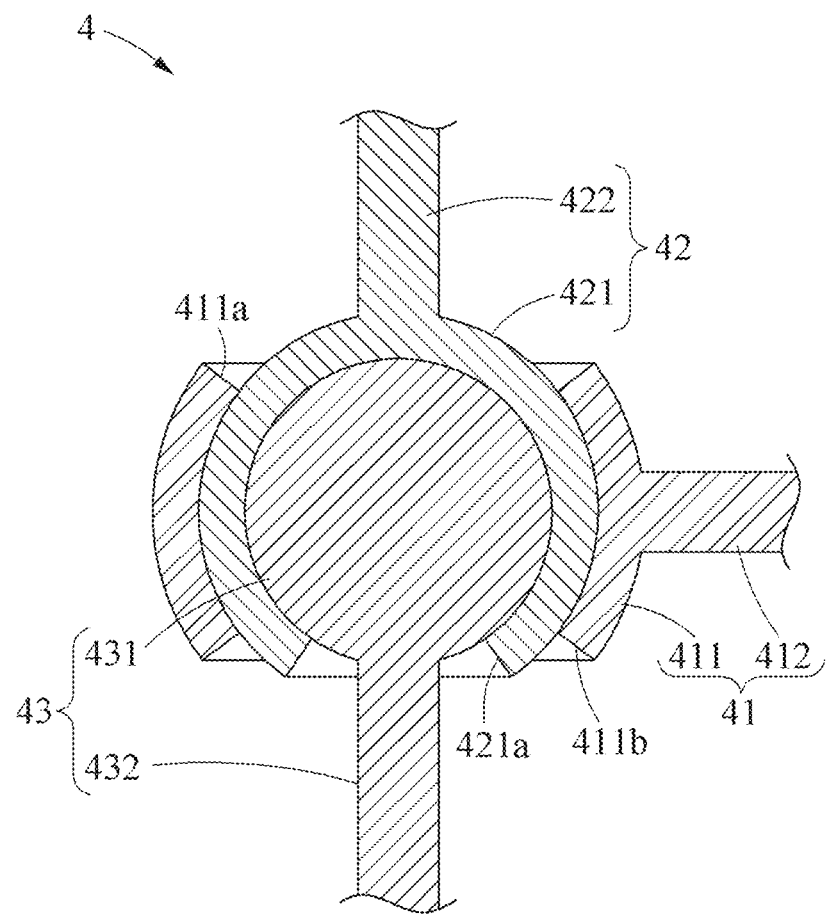
FIG. 14 is a cross-sectional view illustrating the link assembly of FIG. 13.

FIG. 13 is a top view illustrating a link assembly according to at least one example embodiment, and FIG. 14 is a cross-sectional view illustrating the link assembly of FIG. 13.

Referring to FIGS. 13 and 14, a link assembly 4 may include a base link 41, an input link 42, and an output link 43. The base link 41 and the input link 42 may be connected in a ball joint manner. Similarly, the input link 42 and the output link 43 may be connected in a ball joint manner.

The base link 41 may include a base head 411 and a base body 412. The base head 411 may include a space to receive at least a portion of the input link 42. A gasket (not shown) to reduce a friction with the input link 42 may be provided on an inner wall of the base head 411.

The base link 41 may include a first opening hall 411a formed on one side of the base head 411 and enclosing the input link 42. The first opening hall 411a may set a range of motion of the input link 42. Further, the base link 41 may include a second opening hall 411b formed on the other side of the base head 411 and enclosing the output link 43. The second opening hall 411b may set a range of motion of the output link 43.

The input link 42 may perform an at least 2-DOF rotational motion with respect to the base link 41. A center of rotation of the input link 42 may be positioned inside of the base head 411. The input link 42 may include an input head 421 configured to roll inside of the base head 411, and an input body 422 extending from the input head 421. The input head 421 may has an approximately spherical shape. The input head 421 may include a space to receive at least a portion of the output link 43. A gasket (not shown) to reduce a friction with the output link 43 may be provided on an inner wall of the input head 421. The input head 421 may include a third opening hall 421a enclosing the output link 43.

The output link 43 may perform an at least 2-DOF rotational motion with respect to the input link 42. A center of rotation of the output link 43 may be positioned inside of the input head 421. The output link 43 may include an output head 431 configured to roll inside of the input head 421, and an output body 432 extending from the output head 431. The output head 431 may have an approximately spherical shape.

FIGS. 13 and 14 illustrate an example in which the base head 411 is an outermost head and the output head 431 is an innermost head, among the base head 411, the input head 421, and the output head 431. However, example embodiments are not limited thereto. For example, the input head 421 may be an outermost head, and the base head 411 may be positioned between the input head 421 and the output head 431.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A link assembly configured to transmit a power from a driver of a motion assistance apparatus to a distal support of the motion assistance apparatus that supports a distal part of a user, the link assembly comprising:
a main frame;
an output link including a first end and a second end, the first end of the output link connected to the distal support and the second end of the output link rotatably connected to the main frame, the output link configured to rotate within an interior of the main frame such that the output link is configured to perform at least 2-degree of freedom (DOF) rotation with respect to the main frame about a center of rotation of the output link; and
a base link and an input link each including a first end and a second end, the first end of the base link being rotatably connected to a proximal support of the motion assistance apparatus and the first end of the input link being configured to receive the power from the driver, wherein
the second end of each of the output link, the base link and the input link are each rotatably connected to the main frame to form a spherical shaped ball joint such that axes of rotation of the main frame with respect to each of the base link and the input link pass through the center of rotation of the output link.

2. The link assembly of claim 1, wherein a center of rotation of the output link is inside of the main frame.

3. The link assembly of claim 1, wherein the output link comprises:
an output head connected to an interior of the main frame via a ball joint; and
an output body extending from the output head.

4. The link assembly of claim 1, further comprising:
a rotary frame rotatably connected to an interior of the main frame, the rotary frame configured to rotatably support the output link.

5. A link assembly configured to transmit a power from a driver of a motion assistance apparatus to a distal support of the motion assistance apparatus that supports a distal part of a user, the link assembly comprising:
a base link including a first end and a second end, the first end of the base link being rotatably connected to a proximal support of the motion assistance apparatus and the second end of the base link including a base head;
an input link including a first end and a second end, the first end of the input link configured to receive the power from the driver and the second end of the input link including an input head connected to the base head such that the input head is configured to perform at least 2-degree of freedom (DOF) rotational motion about the base head; and
an output link including a first end and a second end, the first end of the output link connected to the distal support and the second end of the output link having an output head connected to the base link or the input link such that the output link is configured to perform at least 2-DOF rotational motion about the base head about a center of rotation of the output link, wherein
the base head, the input head and the output head form a spherical shaped ball joint such that axes of rotation of the base link and the input link each pass through the center of rotation of the output link.

6. The link assembly of claim 5, wherein the input link comprises:
the input head connected to the base head via a ball joint; and
an input body extending from the input head.

7. The link assembly of claim 6, further comprising:
a rotary frame rotatably connected to an interior of the input head, the rotary frame configured to rotatably support the output link.

8. The link assembly of claim 6, wherein the output link comprises:
the output head connected to the base head or the input head via a ball joint; and
an output body extending from the output head.

9. The link assembly of claim 8, wherein
an outermost head among the base head, the input head, and the output head has two opposing walls, and
a middle head among the base head, the input head, and the output head has a single wall.

10. A motion assistance apparatus comprising:
a proximal support configured to support a proximal part of a user;
a distal support configured to support a distal part of the user;
a driver connected to the proximal support; and a link assembly configured to transmit a power from the driver to the distal support, the link assembly including,
a main frame,
a base link including a first end rotatably connected to the proximal support and a second end rotatably connected to the main frame,
an input link including a first end configured to receive the power from the driver and a second end rotatably connected to the main frame, and
an output link including a first end rotatably connected to the main frame and a second end connected to the distal support such that the output link is configured to perform at least 2-degree of freedom (DOF) rotation with respect to the main frame.

11. The motion assistance apparatus of claim 10, wherein the link assembly further comprises:
a fixed link fixed to the proximal support, the fixed link configured to rotatably support the base link;
a connecting link between the fixed link and the main frame, the connecting link rotatably connected to the base link; and
an auxiliary link rotatably connected to the fixed link and the connecting link.

12. The motion assistance apparatus of claim 11, wherein the distal support is configured to rotate about a remote center of motion (RCM).

13. The motion assistance apparatus of claim 10, wherein a center of rotation of the output link with respect to the main frame is inside of the main frame.

14. The motion assistance apparatus of claim 10, wherein the output link comprises:
an output head connected to the main frame via a ball joint; and
an output body extending from the output head.

15. The motion assistance apparatus of claim 10, wherein the link assembly further comprises:
a rotary frame rotatably connected to an interior of the main frame, the rotary frame configured to rotatably support the output link.

16. A motion assistance apparatus comprising:
a proximal support configured to support a proximal part of a user;
a distal support configured to support a distal part of the user;
a driver connected to the proximal support; and
a link assembly configured to transmit a power from the driver to the distal support, the link assembly including,
a base link including a first end rotatably connected to the proximal support, the base link including a base head,
an input link including a first end configured to receive the power received from the driver and a second end connected to the base head such that the second end is configured to perform an at least 2-degree of freedom (DOF) rotational motion about the base head, and
an output link including a first end connected to the base link or the input link and a second end connected to the distal support, the output link configured to perform an at least 2-DOF rotational motion about the base head.

17. The motion assistance apparatus of claim 16, wherein the input link comprises:
an input head connected to the base head via a ball joint; and
an input body extending from the input head.

* * * * *